(12) United States Patent
Rapecki et al.

(10) Patent No.: US 8,435,761 B2
(45) Date of Patent: May 7, 2013

(54) DNA ENCODING ANTIBODY MOLECULES WHICH BIND HUMAN IL-17

(75) Inventors: Stephen Edward Rapecki, Slough (GB); Andrew George Popplewell, Slough (GB); Ralph Adams, Slough (GB)

(73) Assignee: UCB Pharma SA (BE)

( * ) Notice: Subject to any disclaimer, the term of this patent is extended or adjusted under 35 U.S.C. 154(b) by 0 days.

(21) Appl. No.: 13/242,429

(22) Filed: Sep. 23, 2011

(65) Prior Publication Data

US 2012/0129219 A1 May 24, 2012

Related U.S. Application Data

(62) Division of application No. 12/306,251, filed as application No. PCT/GB2007/002370 on Jun. 25, 2007, now Pat. No. 8,057,794.

(30) Foreign Application Priority Data

Jun. 29, 2006 (GB) .................................. 0612928.2

(51) Int. Cl.
*C12P 21/08* (2006.01)

(52) U.S. Cl.
USPC ............... 435/69.6; 536/23.53; 435/320.1; 435/325; 435/6.1; 530/388.23

(58) Field of Classification Search ............. None
See application file for complete search history.

(56) References Cited

U.S. PATENT DOCUMENTS

| | | | |
|---|---|---|---|
| 2007/0009959 A1 | 1/2007 | Lawson et al. | |
| 2008/0181888 A1 | 7/2008 | Ambrose et al. | |

FOREIGN PATENT DOCUMENTS

| | | |
|---|---|---|
| WO | WO 00/69463 | 11/2000 |
| WO | WO 2004/106377 | 12/2004 |
| WO | WO 2005/001044 | 2/2005 |
| WO | WO 2005/051422 | 6/2005 |
| WO | WO 2006/013107 | 2/2006 |
| WO | WO 2006/054059 | 5/2006 |
| WO | WO 2006/088833 | 8/2006 |
| WO | WO 2007/070750 | 6/2007 |
| WO | WO 2007/106769 | 9/2007 |
| WO | WO 2007/149032 | 12/2007 |
| WO | WO 2008/001063 | 1/2008 |
| WO | WO 2008/021156 | 2/2008 |
| WO | WO 2008/047134 | 4/2008 |

OTHER PUBLICATIONS

PCT International Search Report of PCT International Application PCT/GB2009/001026 filed Apr. 22, 2009.
PCT International Search Report of PCT International Application PCT/GB07/003983 filed Oct. 18, 2007.
Holt, Lucy J.: Domain Antibodies: Proteins for Therapy, Trends in Biotechnology, Nov. 2003, pp. 484-490, vol. 21, No. 11.
Davies, Julian, Affinity Improvement of Single Antibody VH Domains: Residues in All Three Hypervariable Regions Affect Antigen Binding, Sep. 1996, pp. 169-179, vol. 2, No. 3.
Anti-human IL-17 Antibody, R& D Systems, Aug. 28, 2007, retrieved from internet: http://www.mdsystems, com/pdf/af317na. pdf on Mar. 27, 2008.
PCT International Search Report of PCT International Application PCT/GB2005/004392, dated Feb. 14, 2006.
Chabaud, M., et al, "Contribution of Interleukin 17 to Synovium Matrix Destruction in Rheumatoid Arthritis," Cytokine, Academic Press Ltd., vol. 12, No. 7, Jul. 2000, pp. 1092-1099.
Chung, et al, "CD4+ T cells regulate surgical and postinfection adhesion formation," The Journal of Experimental Medicine, Jun. 3, 2002, vol. 195, No. 11, Jun. 3, 2002, pp. 1471-1478.
Dumont, F. J., "IL-17 cytokine/receptor families: Emerging targets for the modulation of inflammatory responses," Expert Opinion of Therapeutic Patents, Ashley Publications, GB vol. 13, No. 3, Mar. 1, 2003, pp. 287-3030.
Hellings, et al., "Interleukin-17 orchestrates the granulocyte influx into airways after allergen inhalation in a mouse model of allergic asthma," American Journal of Respiratory Cell and Molecular Biology, vol. 28, No. 1, Jan. 2003, pp. 42-50.
Numasaki, et al., "Interleukin-17 promotes angiogenesis and tumor growth," Blood, vol. 101, No. 7, Apr. 1, 2003, pp. 2620-2627.
Paul, "Fv Structure and Diversity in Three Dimensions," Fundamental Immunology, 3rd Edition, 1993, pp. 292-295.
Thompson, et al, "Affinity maturation of a high-affinity human monoclonal antibody against the third hypervariable loop of human immunodeficiency virus: use of phage display to improve affinity and broaden strain reactivity," Journal of Molecular biology, vol. 256, No. 1, Feb. 16, 1996, pp. 77-88.
Vandamme, et al, "Contruction and characterization of a recombinant murine monoclonal antibody directed against human fibrin fragment-D dimer," J. Biochem. (1990) vol. 192, pp. 767-775.
Pascalis, et al, "Grafting of 'abbreviated' complementarity-determining regions containing specificity-determining residues essential for ligand contact to engineer a less immunogenic humanized monoclonal antibody," J. Immunol. 2002, 169:3076-3084.

*Primary Examiner* — Dong Jiang
(74) *Attorney, Agent, or Firm* — McDonnell Boehnen Hulbert & Berghoff

(57) ABSTRACT

The invention relates to antibody molecules having specificity for antigenic determinants of IL-17, therapeutic uses of the antibody molecules and methods of producing the antibody molecules.

6 Claims, 6 Drawing Sheets

Figure 1

Figure 2:
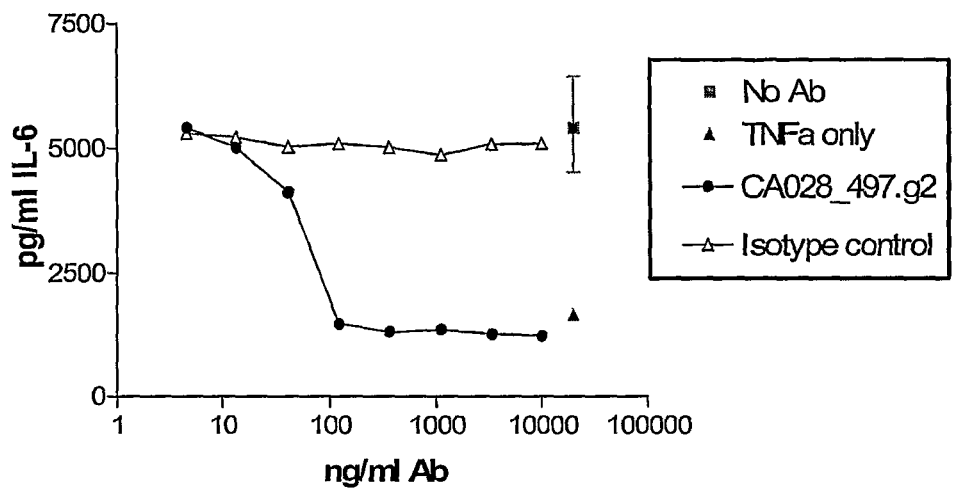

(a) Light Chain variable region of antibody CA048_497.g2 (SEQ ID NO:7)
AIQLTQSPSSLSASVGDRVTITCKASESVSSSMYSYMHWYQQKPGKAPKLLIYRASNLESGV
PSRFSGSGSGTDFTLTISSLQPEDFATYYCQQSWTAPRTFGQGTKVEIKR (b) Heavy chain variable region of antibody CA048_497.g2 (SEQ ID NO:9)
EVQLVESGGGLVKPGGSLRLSCAASGVIFSDYYMAWVRQAPGKGLEWVASINFNADISYYRE
SVKGRFTISRDDSKNTLYLQMNSLKTEDTAVYYCTTDANRQNYDWFAYWGQGTLVTVSS (c)
| | |
|---|---|
| CDRH1: | GVIFSDYYMA (SEQ ID NO:1) |
| CDRH2: | SINFNADISYYRESVKG (SEQ ID NO:2) |
| CDRH3: | DANRQNYDWFAY (SEQ ID NO:3) |
| CDRL1: | KASESVSSSMYSYMH (SEQ ID NO:4) |
| CDRL2: | RASNLES (SEQ ID NO:5) |
| CDRL3: | QQSWTAPRT (SEQ ID NO:6) |

(d) Light chain of antibody CA048_497.g2 (SEQ ID NO:11)

AIQLTQSPSSLSASVGDRVTITCKASESVSSSMYSYMHWYQQKPGKAPKLLIYRASNLESGV
PSRFSGSGSGTDFTLTISSLQPEDFATYYCQQSWTAPRTFGQGTKVEIKRTVAAPSVFIFPP
SDEQLKSGTASVVCLLNNFYPREAKVQWKVDNALQSGNSQESVTEQDSKDSTYSLSSTLTLS
KADYEKHKVYACEVTHQGLSSPVTKSFNRGEC (e) Light chain of antibody CA048_497.g2 including signal sequence (SEQ ID NO:12)

MSVPTQVLGLLLLWLTDARCAIQLTQSPSSLSASVGDRVTITCKASESVSSSMYSYMHWYQQ
KPGKAPKLLIYRASNLESGVPSRFSGSGSGTDFTLTISSLQPEDFATYYCQQSWTAPRTFGQ
GTKVEIKRTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (f) Heavy chain of antibody CA048_497.g2 (SEQ ID NO:15)

EVQLVESGGGLVKPGGSLRLSCAASGVIFSDYYMAWVRQAPGKGLEWVASINFNADISYYRE
SVKGRFTISRDDSKNTLYLQMNSLKTEDTAVYYCTTDANRQNYDWFAYWGQGTLVTVSSAST
KGPSVFPLAPCSRSTSESTAALGCLVKDYFPEPVTVSWNSGALTSGVHTFPAVLQSSGLYSL
SSVVTVPSSSLGTKTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQFNSTYRVVSVLTVL
HQDWLNGKEYKCKVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGNVFSCSVMHEALH
NHYTQKSLSLSLGK (g) Heavy chain of antibody CA048_497.g2 including signal sequence (SEQ ID NO:16)

<ins>MEWSWVFLFFLSVTTGVHS</ins>EVQLVESGGGLVKPGGSLRLSCAASGVIFSDYYMAWVRQAPGK
GLEWVASINFNADISYYRESVKGRFTISRDDSKNTLYLQMNSLKTEDTAVYYCTTDANRQNY
DWFAYWGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (h) DNA encoding Light chain variable region of antibody CA048_497.g2 (SEQ ID NO:8)
GCCATCCAGCTGACCCAGAGCCCTTCCTCTCTCAGCGCCAGTGTCGGAGACAGAGTGACTATTACCTG
CAAAGCCTCCGAATCAGTCAGTTCCTCTATGTATTCTTATATGCACTGGTACCAGCAAAAGCCCGGAA
AGGCTCCTAAATTGCTGATCTACAGGGCAAGCAACCTCGAGAGCGGCGTGCCCAGCAGGTTCAGCGGC
AGTGGGTCTGGAACTGACTTTACCCTGACAATCTCCTCACTCCAGCCCGAGGACTTCGCCACCTATTA
CTGCCAGCAGAGCTGGACAGCTCCTAGGACATTTGGACAGGGCACTAAAGTGGAAATCAAGCGT (i) DNA encoding Heavy chain variable region of antibody CA048_497.g2 (SEQ ID NO:10)
GAGGTTCAGCTCGTTGAATCCGGAGGCGGACTCGTGAAGCCCGGAGGCAGTCTTCGCTTGTCCTGCGC
TGCATCTGGAGTGATCTTTAGCGATTACTATATGGCTTGGGTGAGACAGGCACCTGGGAAAGGCCTCG
AATGGGTGGCCAGTATTAACTTCAATGCCGACATCAGCTACTATCGAGAGTCTGTGAAGGGTAGATTC
ACAATCTCACGGGATGACAGTAAGAACACACTGTACCTGCAGATGAATTCCCTGAAAACCGAGGATAC
CGCCGTTTACTATTGTACCACTGACGCCAACAGGCAGAATTACGACTGGTTTGCCTATTGGGGCAGG
GCACTCTGGTCACCGTCTCGAGC (j) DNA encoding Light chain of antibody CA048_497.g2 (SEQ ID NO:13)
GCCATCCAGCTGACCCAGAGCCCTTCCTCTCTCAGCGCCAGTGTCGGAGACAGAGTGACTATTACCTG
CAAAGCCTCCGAATCAGTCAGTTCCTCTATGTATTCTTATATGCACTGGTACCAGCAAAAGCCCGGAA
AGGCTCCTAAATTGCTGATCTACAGGGCAAGCAACCTCGAGAGCGGCGTGCCCAGCAGGTTCAGCGGC
AGTGGGTCTGGAACTGACTTTACCCTGACAATCTCCTCACTCCAGCCCGAGGACTTCGCCACCTATTA
CTGCCAGCAGAGCTGGACAGCTCCTAGGACATTTGGACAGGGCACTAAAGTGGAAATCAAGCGTACGG
TAGCGGCCCCATCTGTCTTCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCACCTACAGCCTCAGCAGCA
CCCTGACGCTGAGCAAAGCAGACTACGAGAAACACAAAGTCTACGCCTGCGAAGTCACCCATCAGGGC
CTGAGCTCGCCCGTCACAAAGAGCTTCAACAGGGGAGAGTGTTAG (k) DNA encoding Light chain of antibody CA048_497.g2 including signal sequence (SEQ ID NO:14)
ATGTCAGTTCCCACACAGGTGCTGGGCCTGCTTCTGTTGTGGCTCACCGATGCTAGGTGTGCCATCCA
GCTGACCCAGAGCCCTTCCTCTCTCAGCGCCAGTGTCGGAGACAGAGTGACTATTACCTGCAAAGCCT
CCGAATCAGTCAGTTCCTCTATGTATTCTTATATGCACTGGTACCAGCAAAAGCCCGGAAAGGCTCCT
AAATTGCTGATCTACAGGGCAAGCAACCTCGAGAGCGGCGTGCCCAGCAGGTTCAGCGGCAGTGGGTC
TGGAACTGACTTTACCCTGACAATCTCCTCACTCCAGCCCGAGGACTTCGCCACCTATTACTGCCAGC
AGAGCTGGACAGCTCCTAGGACATTTGGACAGGGCACTAAAGTGGAAATCAAGCGTACGGTAGCGGCC
CCATCTGTCTTCATCTTCCCGCCATCTGATGAGCAGTTGAAATCTGGAACTGCCTCTGTTGTGTGCCT
GCTGAATAACTTCTATCCCAGAGAGGCCAAAGTACAGTGGAAGGTGGATAACGCCCTCCAATCGGGTA
ACTCCCAGGAGAGTGTCACAGAGCAGGACAGCAAGGACAGCACCTACAGCCTCAGCAGCACCCTGACG
CTGAGCAAAGCAGACTACGAGAAACACAAAGTCTACGCCTGCGAAGTCACCCATCAGGGCCTGAGCTC
GCCCGTCACAAAGAGCTTCAACAGGGGAGAGTGTTAG (l) DNA encoding Heavy chain of antibody CA048_497.g2 (SEQ ID NO:17)
GAGGTTCAGCTCGTTGAATCCGGAGGCGGACTCGTGAAGCCCGGAGGCAGTCTTCGCTTGTCCTGCGC
TGCATCTGGAGTGATCTTTAGCGATTACTATATGGCTTGGGTGAGACAGGCACCTGGGAAAGGCCTCG
AATGGGTGGCCAGTATTAACTTCAATGCCGACATCAGCTACTATCGAGAGTCTGTGAAGGGTAGATTC
ACAATCTCACGGGATGACAGTAAGAACACACTGTACCTGCAGATGAATTCCCTGAAAACCGAGGATAC
CGCCGTTTACTATTGTACCACTGACGCCAACAGGCAGAATTACGACTGGTTTGCCTATTGGGGCAGG
GCACTCTGGTCACCGTCTCGAGCGCTTCTACAAAGGGCCCATCCGTCTTCCCCCTGGCGCCCTGCTCC
AGGAGCACCTCCGAGAGCACAGCCGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGCACGAAGACCTACACCTGC
AACGTAGATCACAAGCCCAGCAACACCAAGGTGGACAAGAGAGTTGGTGAGAGGCCAGCACAGGGAGG
GAGGGTGTCTGCTGGAAGCCAGGCTCAGCCCTCCTGCCTGGACGCACCCCGGCTGTGCAGCCCCAGCC
CAGGGCAGCAAGGCATGCCCCATCTGTCTCCTCACCCGGAGGCCTCTGACCACCCCACTCATGCCCAG
GGAGAGGGTCTTCTGGATTTTTCCACCAGGCTCCGGGCAGCCACAGGCTGGATGCCCCTACCCCAGGC
CCTGCGCATACAGGGGCAGGTGCTGCGCTCAGACCTGCCAAGAGCCATATCCGGGAGGACCCTGCCCC
TGACCTAAGCCCACCCCAAAGGCCAAACTCTCCACTCCCTCAGCTCAGACACCTTCTCTCCTCCCAGA
TCTGAGTAACTCCCAATCTTCTCTCTGCAGAGTCCAAATATGGTCCCCCATGCCCACCATGCCCAGGT
AAGCCAACCCAGGCCTCGCCCTCCAGCTCAAGGCGGGACAGGTGCCCTAGAGTAGCCTGCATCCAGGG
ACAGGCCCCAGCCGGGTGCTGACGCATCCACCTCCATCTCTTCCTCAGCACCTGAGTTCCTGGGGGGA
CCATCAGTCTTCCTGTTCCCCCCAAAACCCAAGGACACTCTCATGATCTCCCGGACCCCTGAGGTCAC
GTGCGTGGTGGTGGACGTGAGCCAGGAAGACCCCGAGGTCCAGTTCAACTGGTACGTGGATGGCGTGG
AGGTGCATAATGCCAAGACAAAGCCGCGGGAGGAGCAGTTCAACAGCACGTACCGTGTGGTCAGCGTC
CTCACCGTCCTGCACCAGGACTGGCTGAACGGCAAGGAGTACAAGTGCAAGGTCTCCAACAAAGGCCT
CCCGTCCTCCATCGAGAAAACCATCTCCAAAGCCAAAGGTGGGACCCACGGGGTGCGAGGGCCACATG
GACAGAGGTCAGCTCGGCCCACCCTCTGCCCTGGGAGTGACCGCTGTGCCAACCTCTGTCCCTACAGG
GCAGCCCCGAGAGCCACAGGTGTACACCCTGCCCCCATCCCAGGAGGAGATGACCAAGAACCAGGTCA
GCCTGACCTGCCTGGTCAAAGGCTTCTACCCCAGCGACATCGCCGTGGAGTGGGAGAGCAATGGGCAG
CCGGAGAACAACTACAAGACCACGCCTCCCGTGCTGGACTCCGACGGCTCCTTCTTCCTCTACAGCAG
GCTAACCGTGGACAAGAGCAGGTGGCAGGAGGGGAATGTCTTCTCATGCTCCGTGATGCATGAGGCTC
TGCACAACCACTACACACAGAAGAGCCTCTCCCTGTCTCTGGGTAAATGA (m) DNA encoding Heavy chain of antibody CA048_497.g2 including signal sequence (SEQ ID NO:18)

ATGGAATGGTCCTGGGTCTTCCTGTTTTTCCTTTCTGTCACAACCGGGGTGCACAGCGAGGTTCAGCT
CGTTGAATCCGGAGGCGGACTCGTGAAGCCCGGAGGCAGTCTTCGCTTGTCCTGCGCTGCATCTGGAG
TGATCTTTAGCGATTACTATATGGCTTGGGTGAGACAGGCACCTGGGAAAGGCCTCGAATGGGTGGCC
AGTATTAACTTCAATGCCGACATCAGCTACTATCGAGAGTCTGTGAAGGGTAGATTCACAATCTCACG
GGATGACAGTAAGAACACACTGTACCTGCAGATGAATTCCCTGAAAACCGAGGATACCGCCGTTTACT
ATTGTACCACTGACGCCAACAGGCAGAATTACGACTGGTTTGCCTATTGGGGCAGGGCACTCTGGTC
ACCGTCTCGAGCGCTTCTACAAAGGGCCCATCCGTCTTCCCCCTGGCGCCCTGCTCCAGGAGCACCTC
CGAGAGCACAGCCGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTACACCTGCAACGTAGATCA
CAAGCCCAGCAACACCAAGGTGGACAAGAGAGTTGGTGAGAGGCCAGCACAGGGAGGGAGGGTGTCTG
CTGGAAGCCAGGCTCAGCCCTCCTGCCTGGACGCACCCCGGCTGTGCAGCCCCAGCCCAGGGCAGCAA
GGCATGCCCCATCTGTCTCCTCACCCGGAGGCCTCTGACCACCCCACTCATGCCCAGGGAGAGGGTCT
TCTGGATTTTTCCACCAGGCTCCGGGCAGCCACAGGCTGGATGCCCCTACCCCAGGCCCTGCGCATAC
AGGGGCAGGTGCTGCGCTCAGACCTGCCAAGAGCCATATCCGGGAGGACCCTGCCCCTGACCTAAGCC
CACCCCAAAGGCCAAACTCTCCACTCCCTCAGCTCAGACACCTTCTCTCCTCCCAGATCTGAGTAACT
CCCAATCTTCTCTCTGCAGAGTCCAAATATGGTCCCCATGCCCACCATGCCCAGGTAAGCCAACCCA
GGCCTCGCCCTCCAGCTCAAGGCGGGACAGGTGCCCTAGAGTAGCCTGCATCCAGGGACAGGCCCCAG
CCGGGTGCTGACGCATCCACCTCCATCTCTTCCTCAGCACCTGAGTTCCTGGGGGACCATCAGTCTT
CCTGTTCCCCCCAAAACCCAAGGACACTCTCATGATCTCCCGGACCCCTGAGGTCACGTGCGTGGTGG
TGGACGTGAGCCAGGAAGACCCCGAGGTCCAGTTCAACTGGTACGTGGATGGCGTGGAGGTGCATAAT
GCCAAGACAAAGCCGCGGGAGGAGCAGTTCAACAGCACGTACCGTGTGGTCAGCGTCCTCACCGTCCT
GCACCAGGACTGGCTGAACGGCAAGGAGTACAAGTGCAAGGTCTCCAACAAAGCCTCCCGTCCTCCA
TCGAGAAAACCATCTCCAAAGCCAAAGGTGGGACCCACGGGGTGCGAGGGCCACATGGACAGAGGTCA
GCTCGGCCCACCCTCTGCCCTGGGAGTGACCGCTGTGCCAACCTCTGTCCCTACAGGGCAGCCCCGAG
AGCCACAGGTGTACACCCTGCCCCCATCCCAGGAGGAGATGACCAAGAACCAGGTCAGCCTGACCTGC
CTGGTCAAAGGCTTCTACCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTACAGCAGGCTAACCGTGG
ACAAGAGCAGGTGGCAGGAGGGGAATGTCTTCTCATGCTCCGTGATGCATGAGGCTCTGCACAACCAC
TACACACAGAAGAGCCTCTCCCTGTCTCTGGGTAAATGA

DNA ENCODING ANTIBODY MOLECULES WHICH BIND HUMAN IL-17

CROSS-REFERENCE TO RELATED APPLICATIONS

This application is a divisional application of U.S. patent application Ser. No. 12/306,251, filed Oct. 27, 2009, now U.S. Pat. No. 8,057,794, issued Nov. 15, 2011, which claims the benefit of priority to and incorporates by reference PCT Application Serial No. PCT/GB07/002,370, filed Jun. 25, 2007.

The present invention relates to antibody molecules having specificity for antigenic determinants of IL-17. The present invention also relates to the therapeutic uses of the antibody molecules and methods for producing said antibody molecules.

Interleukin 17 (IL-17), also known as CTLA-8 or IL-17A, is a pro-inflammatory cytokine which stimulates the secretion of a wide range of other cytokines from various non-immune cells. IL-17 is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17 is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177 (11); 36-39). A number of homologues of IL-17 have been identified which have both similar and distinct roles in regulating inflammatory responses. For a review of IL-17 cytokine/receptor families see Dumont, 2003, Expert Opin. Ther. Patents, 13, 287-303.

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art for example a murine IL-17R:human Fc fusion protein, a murine soluble IL-17R and an anti-IL-17 monoclonal antibody have been used to demonstrate the role of IL-17 in various models of rheumatoid arthritis (Lubberts et al., J. Immunol. 2001, 167, 1004-1013; Chabaud et al., Arthritis Res. 2001, 3, 168-177). In addition, neutralising polyclonal antibodies have been used to reduce peritoneal adhesion formation (Chung et al., 2002, J. Exp. Med., 195, 1471-1478). Rat derived anti-human IL-17 antibodies were described in WO04/106377. A humanised anti-IL-17 antibody with an affinity of around 220 pM was described in WO2006/054059. A monoclonal anti-IL-17 fully human antibody with an affinity of around 188 pM was described in WO2006/013107.

There is still a need in the art for an improved anti-IL-17 antibody suitable for treating patients.

We have now identified a high affinity neutralising anti-IL-17 antibody suitable for use in the treatment or prophylaxis of pathological disorders mediated by IL-17 or associated with an increased level of IL-17.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'neutralising antibody' describes an antibody that is capable of neutralising the biological signalling activity of IL-17, for example by blocking binding of IL-17 to one or more of its receptors.

Antibodies for use in the present invention may be obtained using any suitable method known in the art. The IL-17 polypeptide or cells expressing the polypeptide can be used to produce antibodies which specifically recognise IL-17. The IL-17 polypeptide may be the 'mature' polypeptide or a biologically active fragment or derivatives thereof. Preferably the IL-17 polypeptide is the mature human polypeptide. IL-17 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-17 polypeptide may in some instances be part of a larger protein such as a fusion protein for example fused to an affinity tag. Antibodies generated against the IL-17 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93 (15):7843-78481; WO92/02551; WO2004/051268 and International Patent Application number WO2004/106377.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are those antibodies encoded by immunoglobulin genes that have been genetically engineered so that the light and heavy chain genes are composed of immunoglobulin gene segments belonging to different species.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts eg. as described in general terms in EP0546073 B1, U.S. Pat. Nos. 5,545,806, 5,569,825, 5,625, 126, 5,633,425, 5,661,016, 5,770,429, EP 0438474 B1 and EP0463151 B1.

In one embodiment the present invention provides a neutralising antibody having specificity for human IL-17, comprising a heavy chain, wherein the variable domain of the heavy chain comprises at least one of a CDR having the sequence given in FIG. 1 (c) SEQ ID NO:1 for CDR-H1, a CDR having the sequence given in FIG. 1(c) SEQ ID NO:2 for CDR-H2 and a CDR having the sequence given in FIG. 1(c) SEQ ID NO:3 for CDR-H3.

In another embodiment the present invention provides a neutralising antibody having specificity for human IL-17, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment the present invention provides a neutralising antibody having specificity for human IL-17, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In one embodiment the present invention provides a neutralising antibody having specificity for human IL-17, comprising a light chain, wherein the variable domain of the light chain comprises at least one of a CDR having the sequence given in FIG. 1 (c) SEQ ID NO:4 for CDR-L1, a CDR having the sequence given in FIG. 1 (c) SEQ ID NO:5 for CDR-L2 and a CDR having the sequence given in FIG. 1 (c) SEQ ID NO:6 for CDR-L3.

In another embodiment the present invention provides a neutralising antibody having specificity for human IL-17, comprising a light chain, wherein at least two of CDR-L1, CDR-L2 and CDR-L3 of the variable domain of the light chain are selected from the following: the sequence given in SEQ ID NO:4 for CDR-L1, the sequence given in SEQ ID NO:5 for CDR-L2 and the sequence given in SEQ ID NO:6 for CDR-L3. For example, the antibody may comprise a light chain wherein CDR-L1 has the sequence given in SEQ ID NO:4 and CDR-L2 has the sequence given in SEQ ID NO:5. Alternatively, the antibody may comprise a light chain wherein CDR-L1 has the sequence given in SEQ ID NO:4 and CDR-L3 has the sequence given in SEQ ID NO:6, or the antibody may comprise a light chain wherein CDR-L2 has the sequence given in SEQ ID NO:5 and CDR-L3 has the sequence given in SEQ ID NO:6. For the avoidance of doubt, it is understood that all permutations are included.

In another embodiment the present invention provides a neutralising antibody having specificity for human IL-17, comprising a light chain, wherein the variable domain comprises the sequence given in SEQ ID NO:4 for CDR-L1, the sequence given in SEQ ID NO:5 for CDR-L2 and the sequence given in SEQ ID NO:6 for CDR-L3.

The antibody molecules of the present invention preferably comprise a complementary light chain or a complementary heavy chain, respectively.

Hence in one embodiment, an antibody according to the present invention comprises a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and a light chain wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3.

It will be appreciated that one or more amino acid substitutions, additions and/or deletions may be made to the CDRs provided by the present invention without significantly altering the ability of the antibody to bind to IL-17 and to neutralise IL-17 activity. The effect of any amino acid substitutions, additions and/or deletions can be readily tested by one skilled in the art, for example by using the methods described in the Examples to determine IL-17 binding and neutralisation. Accordingly, the present invention provides an antibody having specificity for human IL-17 comprising one or more CDRs selected from CDRH-1 (SEQ ID NO:1), CDRH-2 (SEQ ID NO:2), CDRH-3 (SEQ ID NO:3), CDRL-1 (SEQ ID NO:4), CDRL-2 (SEQ ID NO:5) and CDRL-3 (SEQ ID NO:6) in which one or more amino acids in one or more of the CDRs has been substituted with another amino acid, preferably a similar amino acid as defined herein below. In one embodiment, the present invention provides an antibody having specificity for human IL-17 comprising CDRH-1 (SEQ ID NO:1), CDRH-2 (SEQ ID NO:2), CDRH-3 (SEQ ID NO:3), CDRL-1 (SEQ ID NO:4), CDRL-2 (SEQ ID NO:5) and CDRL-3 (SEQ ID NO:6) as shown in FIG. 1(c) in which one or more amino acids in one or more of the CDRs has been substituted with another amino acid, preferably a similar amino acid as defined herein below.

In one embodiment, an antibody of the present invention comprises a heavy chain, wherein the variable domain of the heavy chain comprises three CDRs wherein the sequence of CDRH-1 has at least 60% identity or similarity to the sequence given in SEQ ID NO:1, CDRH-2 has at least 60% identity or similarity to the sequence given in SEQ ID NO:2 and/or CDRH-3 has at least 60% identity or similarity to the sequence given in SEQ ID NO:3. In another embodiment, an antibody of the present invention comprises a heavy chain, wherein the variable domain of the heavy chain comprises three CDRs wherein the sequence of CDRH-1 has at least 70%, 80%, 90%, 95% or 98% identity or similarity to the sequence given in SEQ ID NO:1, CDRH-2 has at least 70%, 80%, 90%, 95% or 98% identity or similarity to the sequence given in SEQ ID NO:2 and/or CDRH-3 has at least 70%, 80%, 90%, 95% or 98% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, B. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In another embodiment, an antibody of the present invention comprises a light chain, wherein the variable domain of the light chain comprises three CDRs wherein the sequence of CDRL-1 has at least 60% identity or similarity to the sequence given in SEQ ID NO:4, CDRL-2 has at least 60% identity or similarity to the sequence given in SEQ ID NO:5 and/or CDRL-3 has at least 60% identity or similarity to the sequence given in SEQ ID NO:6. In another embodiment, an antibody of the present invention comprises a light chain, wherein the variable domain of the light chain comprises three CDRs wherein the sequence of CDRL-1 has at least 70%, 80%, 90%, 95% or 98% identity or similarity to the sequence given in SEQ ID NO:4, CDRL-2 has at least 70%, 80%, 90%, 95% or 98% identity or similarity to the sequence given in SEQ ID NO:5 and/or CDRL-3 has at least 70%, 80%, 90%, 95% or 98% identity or similarity to the sequence given in SEQ ID NO:6.

In one embodiment the antibody provided by the present invention is a monoclonal antibody.

In one embodiment the antibody provided by the present invention is a chimeric antibody.

In one embodiment the antibody provided by the present invention is a CDR-grafted antibody molecule comprising one or more of the CDRs provided in SEQ ID NOS:1 to 6 (FIG. 1 (c)) or variants thereof. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Preferably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEL LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 1-U 3-15 together with JH4. Accordingly, provided is a neutralising CDR-grafted antibody comprising at least one non-human donor CDR wherein the heavy chain framework region is derived from the human subgroup sequence 1-U 3-15 together with JH4. The sequence of human JH4 is as follows: (YFDY) WGQGTLVTVSS. The YFDY motif is part of CDR-H3 and is not part of framework 4 (Ravetch, J V. et al., 1981, Cell, 27, 583-591).

The preferred framework region for the light chain of the CDR-grafted antibody of the present invention is derived from the human germline sub-group VK1 sequence 2-1-(1) L4 together with JK1. Accordingly, provided is a neutralising CDR-grafted antibody comprising at least one non-human donor CDR wherein the light chain framework region is derived from the human subgroup sequence VK1 2-1-(1) L4 together with JK1. The JK1 sequence is as follows: (WT) FGQGTKVEIK. The WT motif is part of CDR-L3 and is not part of framework 4 (Hieter, P A., et al., 1982, J. Biol. Chem., 257, 1516-1522).

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human VH3 sequence 1-U 3-15 together with JH4, then the acceptor framework regions of the heavy chain comprise, in addition to one or more donor CDRs, a donor residue at at least position 49 (according to Kabat et al., (supra)). Accordingly, provided is a CDR-grafted antibody, wherein at least the residue at position 49 of the variable domain of the heavy chain is a donor residue.

Preferably, in a CDR-grafted antibody molecule according to the present invention, if the acceptor light chain has the human sub-group VK1 sequence 2-1-(1) L4 together with JK1, then no donor residues are transferred i.e. only the CDRs are transferred. Accordingly, provided is a CDR-grafted antibody wherein only the CDRs are transferred to the donor framework.

Donor residues are residues from the donor antibody, i.e. the antibody from which the CDRs were originally derived.

In one embodiment, an antibody of the present invention comprises a heavy chain, wherein the variable domain of the heavy chain comprises the sequence given in FIG. 1 (b) SEQ ID NO:9.

It will be appreciated that one or more amino acid substitutions, additions and/or deletions may be made to the antibody variable domains provided by the present invention without significantly altering the ability of the antibody to bind to IL-17 and to neutralise IL-17 activity. The effect of any amino acid substitutions, additions and/or deletions can be readily tested by one skilled in the art, for example by using the methods described in the Examples to determine IL-17 binding and neutralisation.

In another embodiment, an antibody of the present invention comprises a heavy chain, wherein the variable domain of the heavy chain comprises a sequence having at least 60% identity or similarity to the sequence given in SEQ ID NO:9. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO:9.

In one embodiment, an antibody of the present invention comprises a light chain, wherein the variable domain of the light chain comprises the sequence given in FIG. 1 (a) SEQ ID NO:7.

In another embodiment, an antibody of the present invention comprises a light chain, wherein the variable domain of the light chain comprises a sequence having at least 60% identity or similarity to the sequence given in SEQ ID NO:7. In one embodiment the antibody of the present invention comprises a light chain, wherein the variable domain of the light chain comprises a sequence having at least 70%, 80%, 90%, 95% or 98% identity or similarity to the sequence given in SEQ ID NO:7.

In one embodiment an antibody of the present invention comprises a heavy chain, wherein the variable domain of the heavy chain comprises the sequence given in SEQ ID NO:9 and a light chain, wherein the variable domain of the light chain comprises the sequence given in SEQ ID NO:7.

In another embodiment of the invention, the antibody comprises a heavy chain and a light chain, wherein the variable domain of the heavy chain comprises a sequence having at least 60% identity or similarity to the sequence given in SEQ ID NO:9 and the variable domain of the light chain comprises a sequence having at least 60% identity or similarity to the sequence given in SEQ ID NO:7. Preferably, the antibody comprises a heavy chain, wherein the variable domain of the heavy chain comprises a sequence having at least 70%, 80%, 90%, 95% or 98% identity or similarity to the sequence given in SEQ ID NO:9 and a light chain, wherein the variable domain of the light chain comprises a sequence having at least 70%, 80%, 90%, 95% or 98% identity or similarity to the sequence given in SEQ ID NO:7.

The antibody molecules of the present invention may comprise a complete antibody molecule having full length heavy and light chains or a fragment thereof and may be, but are not limited to Fab, modified Fab, Fab', F(ab')$_2$, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23 (9):1126-1136; Adair and Lawson, 2005, Drug Design Reviews—Online 2 (3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities or may be monospecific (see for example WO 92/22853 and WO05/113605).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. Particularly preferred is the IgG4 constant domain comprising this change. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R. J. *Journal of Chromatography* 705:129-134, 1995). Accordingly, the C-terminal lysine of the antibody heavy chain given in FIG. 1 (*f*), SEQ ID NO: 15 may be absent.

In one embodiment the antibody heavy chain comprises a CH1 domain and the antibody light chain comprises a CL domain, either kappa or lambda.

In a preferred embodiment the antibody provided by the present invention is a neutralising antibody having specificity for human IL-17 in which the heavy chain constant region comprises the human IgG4 constant region in which the serine at position 241 has been substituted by proline as described in Angal et al., supra. Accordingly, the present invention provides an antibody in which the heavy chain comprises or consists of the sequence given in FIG. 1 (*f*), SEQ ID NO:15.

It will be appreciated that one or more amino acid substitutions, additions and/or deletions may be made to the antibody variable and/or constant domains provided by the present invention without significantly altering the ability of the antibody to bind to IL-17 and to neutralise IL-17 activity. The effect of any amino acid substitutions, additions and/or deletions can be readily tested by one skilled in the art, for example by using the methods described in the Examples to determine IL-17 binding and neutralisation.

In one embodiment of the invention, the antibody comprises a heavy chain, wherein the heavy chain comprises a sequence having at least 60% identity or similarity to the sequence given in SEQ ID NO:15. Preferably, the antibody comprises a heavy chain, wherein the heavy chain comprises a sequence having at least 70%, 80%, 90%, 95% or 98% identity or similarity to the sequence given in SEQ ID NO:15.

In one embodiment an antibody molecule according to the present invention comprises a light chain comprising the sequence given in FIG. 1 (*d*), SEQ ID NO:11.

In one embodiment of the invention, the antibody comprises a light chain, wherein the light chain comprises a sequence having at least 60% identity or similarity to the sequence given in SEQ ID NO:11. Preferably, the antibody comprises a light chain, wherein the light chain comprises a sequence having at least 70%, 80%, 90%, 95% or 98% identity or similarity to the sequence given in SEQ ID NO:11.

In one embodiment the present invention provides an antibody in which the heavy chain comprises or consists of the sequence given in SEQ ID NO:15 and the light chain comprises or consists of the sequence given in SEQ ID NO:11.

In one embodiment of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:11. Preferably, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:11.

Also provided by the present invention is a specific region or epitope of human IL-17 which is bound by an antibody provided by the present invention, in particular an antibody comprising the heavy chain sequence gH4 (SEQ ID NO:9) and/or the light chain sequence gL2 (SEQ ID NO:7).

This specific region or epitope of the human IL-17 polypeptide can be identified by any suitable epitope mapping method known in the art in combination with any one of the antibodies provided by the present invention. Examples of such methods include screening peptides of varying lengths derived from IL-17 for binding to the antibody of the present invention with the smallest fragment that can specifically bind to the antibody containing the sequence of the epitope recognised by the antibody. The IL-17 peptides may be produced synthetically or by proteolytic digestion of the IL-17 polypeptide. Peptides that bind the antibody can be identified by, for example, mass spectrometric analysis. In another example, NMR spectroscopy can be used to identify the epitope bound by an antibody of the present invention. Once identified, the epitopic fragment which binds an antibody of the present invention can be used, if required, as an immunogen to obtain additional neutralising antibodies which bind the same epitope.

Antibodies which cross-block the binding of an antibody according to the present invention in particular, an antibody comprising the heavy chain sequence gH4 (SEQ ID NO:9) and the light chain sequence gL2 (SEQ ID NO:7) may be similarly useful in neutralising IL-17 activity. Accordingly, the present invention also provides a neutralising antibody having specificity for human IL-17, which cross-blocks the binding of any one of the antibodies described above to human IL-17 and/or is cross-blocked from binding IL-17 by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore where binding of the cross blocking antibody to human IL-17 prevents the binding of an antibody of the present invention or vice versa.

In one embodiment there is provided a neutralising antibody having specificity for human IL-17, which cross-blocks the binding of an antibody whose heavy chain comprises the sequence gH4 (SEQ ID NO:9) and whose light chain comprises the sequence gL2 (SEQ ID NO:7) to human IL-17. In one embodiment the cross-blocking antibodies provided by the present invention inhibit the binding of an antibody comprising the heavy chain sequence gH4 (SEQ ID NO:9) and the light chain sequence gL2 (SEQ ID NO:7) by greater than 80%, preferably by greater than 85%, more preferably by greater than 90%, even more preferably by greater than 95%.

Alternatively or in addition, neutralising antibodies according to this aspect of the invention may be cross-blocked from binding to human IL-17 by an antibody comprising the heavy chain sequence gH4 (SEQ ID NO:9) and the light chain sequence gL2 (SEQ ID NO:7). Also provided therefore is a neutralising antibody molecule having specificity for human IL-17 which is cross-blocked from binding human IL-17 by an antibody comprising the heavy chain sequence gH4 (SEQ ID NO:9) and the light chain sequence gL2 (SEQ ID NO:7). In one embodiment the neutralising antibodies provided by this aspect of the invention are inhibited from binding human IL-17 by an antibody comprising the heavy chain sequence gH4 (SEQ ID NO:9) and the light chain sequence gL2 (SEQ ID NO:7) by greater than 80%, preferably by greater than 85%, more preferably by greater than 90%, even more preferably by greater than 95%.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human IL-17 of 100 pM or better.

The antibody molecules of the present invention preferably have a high binding affinity, preferably picomolar. Affinity may be measured using any suitable method known in the art, including BIAcore as described in the Examples herein using natural or recombinant IL-17. Preferably affinity is measured using recombinant human IL-17 as described in the examples herein. Preferably the antibody molecules of the present invention have a binding affinity of about 200 pM or better. In one embodiment the antibody molecule of the present invention has a binding affinity of about 100 pM or better. In one embodiment the antibody molecule of the present invention has a binding affinity of about 50 pM or better. In one embodiment the antibody molecule of the present invention has a binding affinity of about 20 pM or better. In one embodiment the antibody molecule of the present invention has a binding affinity of about 10 pM or better. In one embodiment the antibody molecule of the present invention is fully human or humanised and has a binding affinity of about 100 pM or better. It will be appreciated that the affinity of antibodies provided by the present invention may be altered using any suitable method known in the art. The present invention therefore also relates to variants of the antibody molecules of the present invention, which have an improved affinity for IL-17. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention neutralise IL-17 activity, for example in the in vitro assays described in the Examples. In one embodiment the present invention provides a neutralising antibody having specificity for human IL-17 which is capable of inhibiting the activity of 0.8 nM human IL-17 by 50% at a concentration of less than 2 nM said inhibitory activity being measured on the IL-17 induced release of IL-6 from Hela cells. In one embodiment the concentration of antibody which inhibits IL-17 by 50% is less than 1 nM. In one embodiment, less than 0.5 nM. In one embodiment the human IL-17 used in the assay is natural human IL-17. In one embodiment the human IL-17 used in the assay is recombinant human IL-17. In one embodiment the neutralising antibody is a humanised or fully human antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Wash. D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides a neutralising antibody molecule having specificity for human IL-17, which is a modified Fab fragment having a heavy chain comprising the sequence given in SEQ ID NO:9 and a light chain comprising the sequence given in SEQ ID NO:7 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in FIG. 1 (*h*) SEQ ID NO:8; FIG. 1 (*i*) SEQ ID NO:10; FIG. 1 (*j*) SEQ ID NO:13; FIG. 1 (*k*) SEQ ID NO:14; FIG. 1 (*l*) SEQ ID NO:17 and FIG. 1 (*m*) SEQ ID NO:18. Nucleotides 1-57 in SEQ ID NO 18 and 1-60 in SEQ ID NO 14 encode the signal peptide sequence from mouse antibody B72.3 (Whittle et al., 1987, Protein Eng. 1 (6) 499-505.) which is cleaved to give a neutralising antibody molecule of the present invention (the signal peptide corresponds to amino acid residues 1-19 in FIG. 1 (*g*) SEQ ID NO: 16 and 1-20 in FIG. 1 (*e*) SEQ ID NO:12 respectively). The present invention also provides an isolated DNA sequence encoding the heavy chain of an antibody of the present invention which comprises SEQ ID NO:17 or SEQ ID N0:18. The present invention also provides an isolated DNA sequence encoding the light chain of an antibody of the present invention which comprises SEQ ID NO:13 or SEQ ID NO:14.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively. Preferably, a vector according to the present invention comprises the sequences given in SEQ ID NO:14 and SEQ ID NO:18. Nucleotides 1-57 in SEQ ID NO 18 and 1-60 in SEQ ID NO 14 encode the signal peptide sequence from mouse antibody B72.3 (residues 1-19 in SEQ ID NO: 16 and 1-20 in SEQ ID NO:12 respectively) which is most preferably cleaved to give a neutralising antibody molecule of the present invention.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides the antibody molecule of the present invention for use in the treatment or prophylaxis of a pathological disorder that is mediated by IL-17 or associated with an increased level of IL-17. Preferably, the pathological condition is selected from the group consisting of infections (viral, bacterial, fungal and parasitic), endotoxic shock associtated with infection, arthritis, rheumatoid arthritis, asthma, pelvic inflammatory disease, Alzheimer's Disease, Crohn's disease, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, osteoarthritis, periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-17 or associated with an increased level of IL-17. Preferably the pathological disorder is rheumatoid arthritis or multiple sclerosis.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-17 in the human or animal body. IL-17 may be circulating in the body or may be present in an undesirably high level localised at a particular site in the body, for example a site of inflammation.

The antibody molecule of the present invention is preferably used for the control of inflammatory disease.

The present invention also provides a method of treating human or animal subjects suffering from or at risk of a disorder mediated by IL-17, the method comprising administering to the subject an effective amount of the antibody molecule of the present invention.

The antibody molecule of the present invention may also be used in diagnosis, for example in the in vivo diagnosis and imaging of disease states involving IL-17.

The present invention is further described by way of illustration only in the following examples, which refer to the accompanying Figures, in which:

FIG. 1:
a) Light chain V region of antibody CA048_497.g2 (277 gL2gH4) (SEQ ID NO:7)
b) Heavy chain V region of antibody CA048_497.g2 (277 gL2gH4) (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody CA048_497.g2 (277 gL2gH4).
d) Light chain of antibody CA048_497.g2 (SEQ ID NO:11)
e) Light chain of antibody CA048_497.g2 including signal sequence (underlined) (SEQ ID NO:12)
f) Heavy chain of antibody CA048_497.g2 (SEQ ID NO:15)
g) Heavy chain of antibody CA048_497.g2 including signal sequence (underlined) (SEQ ID NO:16)
h) DNA encoding light chain variable region of antibody CA048_497.g2 (SEQ ID NO:8)
i) DNA encoding heavy chain variable region of antibody CA048_497.g2 (SEQ ID NO:10)
j) DNA encoding light chain of antibody CA048_497.g2 (SEQ ID NO:13)
k) DNA encoding light chain of antibody CA048_497.g2 including signal sequence (SEQ ID NO:14)
l) DNA encoding heavy chain of antibody CA048_497.g2 (SEQ ID NO:17)
m) DNA encoding heavy chain of antibody CA048_497.g2 including signal sequence (SEQ ID NO:18)

FIG. 2: Inhibition of IL-6 production by antibody CA048_497.g2 in Hela cells stimulated with recombinant human IL-17

Figure 3:
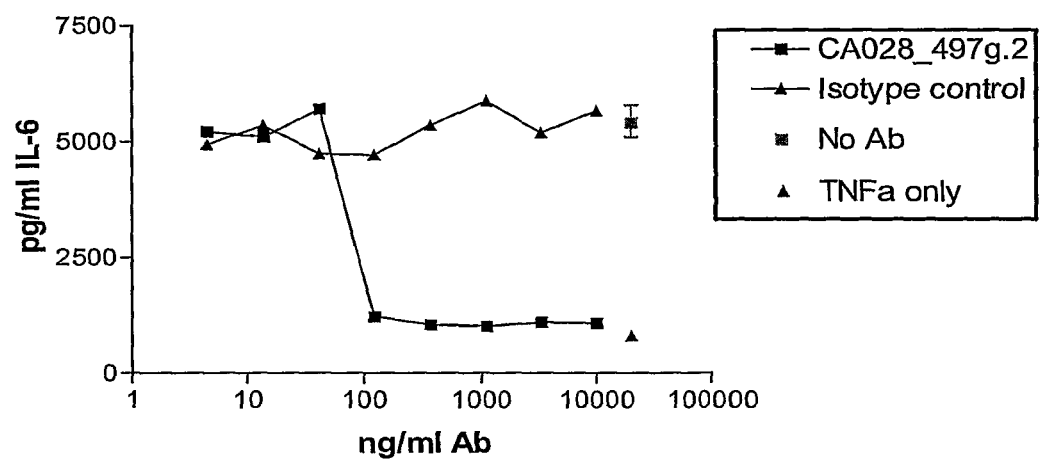

FIG. 3: Inhibition of IL-6 production by antibody CA048 497.g2 in Hela cells stimulated with natural human IL-17

DNA MANIPULATIONS AND GENERAL METHODS

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from Invitrogen. Genes encoding initial V-region sequences were designed and constructed by an automated synthesis approach by Entelechon GmbH, and modified to generate the grafted versions by oligonucleotide directed mutagenesis. The concentration of IgG was determined using IgG assembly ELISA.

EXAMPLE 1

Production of a Neutralising Anti-IL-17 Antibody (Antibody CA048_497.g2 (277 gL2gH4))

Female Sprague Dawly rats were immunised with recombinant human IL-17 (purchased from R & D systems). Rats received four immunisations of 20 µg IL-17 in 100 µl Freund's adjuvant. Antibody 277 which binds human IL-17 was isolated using the methods described in WO04/051268. Genes for the heavy chain variable domain (VH) and light chain variable domain (VL) of antibody 277 were isolated and sequenced following cloning via reverse transcription PCR.

A series of humanised VL and VH regions were designed using human V-region acceptor frameworks and by varying the number of donor residues in the framework regions. Two grafted VL regions (gL1 and 2) and 7 grafted VH regions (gHl-7) were designed and genes were built by oligonucleotide assembly and PCR mutagenesis.

The light chain grafted sequences were sub-cloned into the human light chain expression vector pKH10.1 which contains the DNA encoding the human C-Kappa constant region (Km3 allotype). The heavy chain grafted sequences were sub-cloned into the human gamma-4 expression vector pVhg4P FL, which contains the DNA encoding the human gamma-4 constant region containing the hinge stabilising mutation S241P (Angal et al., supra). Plasmids were co-transfected into CHO cells and the antibodies produced screened for activity in IL-17 binding and neutralisation assays (e.g. IL-17 induced IL-6 production in the cell line 3T3-NIH, based on the method described in Yao et al., J. Immunol. 1995; 155, 5483-5486). Transfections of CHO cells were performed using the Lipofectamine™ 2000 procedure according to manufacturer's instructions (InVitrogen, catalogue No. 11668).

The graft most potent at neutralising IL-17 (gL2gH4) and with the highest expression levels in CHO cells was selected. The V region sequences are shown in FIGS. 1 (a) and (b) and in SEQ ID NOs: 7 and 9 for the light chain (gL2) and heavy chain (gH4) respectively. This antibody was named CA028_497.g2. The CDRs of this antibody are shown in FIG. 1(c). The full-length light and heavy chains are shown in FIGS. 1(d) and (f) respectively. The DNA sequences encoding the light and heavy chains are shown in FIGS. 1(k) and (m) respectively.

The heavy chain acceptor framework is the human germline sequence VH3 1-U 3-15 with framework 4 coming from this portion of the human JR-region germline JH4. The light chain acceptor framework is the human germline sequence VK1 2-1-(1) L4, with framework 4 coming from this portion of the human JK-region germline JK1. The amino acid at position 49 in the heavy chain of SEQ ID NO:9 is a donor residue which was found to be essential for good CHO cell expression and affinity for IL-17.

EXAMPLE 2

Assessment of the Affinity of CA028_497.22 for IL-17

The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass as the analyte binds to the ligand to form a complex on the surface. This corresponds to the association process. The dissociation process is monitored when the analyte is replaced by buffer. The affinity of CA028_497.g2 for IL-17 in the BIAcore assay was assessed with CA028_497.g2 as the ligand and IL-17 as the analyte.

Determination of the Affinity of CA028_497.g2 for IL-17 From Different Species Using CA028_497.g2 as the Ligand Capture of CA028_497.g2 by anti-human IgG Fc immobilised on the sensor chip was followed by titration of human IL-17 or IL-17 from other species, over the captured surface. An example of the procedure is given below:

BIA (Biamolecular Interaction Analysis) was performed using a BIAcore 3000 (BIAcore AB). Affinipure F(ab')$_2$ Fragment goat anti-human IgG, Fc (Jackson ImmunoResearch) was immobilised on a CM5 Sensor Chip via amine coupling chemistry to a capture level of ≈8000 response units (RUs). HBS-EP buffer (10 mM HEPES pH 7.4, 0.15 M NaCl, 3 mM EDTA, 0.005% Surfactant P20, BIAcore AB) was used as the running buffer with a flow rate of 10 µL/min. A 10 µL injection of CA028_497.g2 was used for capture by the immobilised anti-human IgG-F(ab)$_2$. IL-17 was titrated over the captured CA028_497.g2 at various concentrations at a flow rate of 30 µL/min. The surface was regenerated by a 30 µL injection of 40 mM HCl, followed by a 10 µL injection of 5 mM NaOH.

Background subtraction binding curves were analysed using the BIAevaluation software (version 3.2) following standard procedures. Kinetic parameters were determined from the fitting algorithm.

The concentrations of IL-17 from different non-human primate (NHP) species expressed transiently were estimated relative to human IL-17 and these concentrations were then used to determine the affinities of the IL-17s. The affinity was measured at IL-17 concentrations at or below 25 nM. The affinity value determined for CA028_497.g2 was 6.3 pM for human, 10.7 pM for cynomolgus monkey IL-17 and 12.9 pM for marmoset IL-17 (Table 1).

The concentration of transient cynomolgus IL-17 and transient marmoset IL-17 was estimated based on equivalent human IL-17 binding.

TABLE 1

| Affinity of IL-17 for CA028_497.g2 | | | | |
|---|---|---|---|---|
| Reference | $k_a$ (M$^{-1}$s$^{-1}$) | $k_d$ (s$^{-1}$) | $K_d$ (M) | $K_d$ pM |
| Human RnD | 1.86E+06 | 7.38E−06 | 6.28E−12 | 6.3 |
| cynomolgus | 1.57E+06* | 1.68E−05 | 1.07E−11 | 10.7 |
| marmoset 06073130c | 1.13E+06* | 1.46E−05 | 1.29E−10 | 12.9 |

EXAMPLE 3

Neutralisation of Human IL-17 on Human Cells

The ability of IL-17 to induce IL-6 production from human Hela cells was used to determine the neutralising potency of CA028_497.g2 for human recombinant IL-17 and mammalian cell (CHO) derived human IL-17 (termed 'natural' IL-17). Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. 1×10$^4$ cells were plated out into 96 well flat bottomed tissue culture plates. Cells were incubated overnight and washed once in assay buffer. Either human recombinant IL-17 (25 ng ml$^{-1}$) or 'natural' IL-17 (25 ng ml$^{-1}$) was incubated in the presence of a fixed concentration of human TNF-α this mixture was pre-incubated with CA028_497.g2. Cytokine plus antibody was then added to the Hela cells which were incubated overnight. The production of IL-6 in the cell culture supernatant was proportionate to the amount of IL-17 added to the cells. Levels of IL-6 release were determined in the cell supernatants using a Meso Scale Discovery 96-Well Multi-Spot IL-6 Human cytokine assay. Essentially this assay is a sandwich immunoassay, where pre-coated anti-human IL-6 capture antibody binds to IL-6 in the cell supernatants or calibrator solutions, and levels are quantified using an IL-6 specific detection antibody.

CA028_497.g2 potently neutralised human recombinant IL-17 and mammalian cell-derived human IL-17 (FIGS. 2 and 3). The data from these experiments indicates that the IC$_{50}$ of CA028_497g.2 was 51 ng/mL±3 ng/mL (0.34 nM) against human recombinant IL-17 and 103±7 ng/mL (0.7 nM) against mammalian cell-derived IL-17.

It will of course be understood that the present invention has been described by way of example only, is in no way meant to be limiting, and that modifications of detail can be made within the scope of the claims hereinafter. Preferred features of each embodiment of the invention are as for each of the other embodiments *mutatis mutandis*. All publications, including but not limited to patents and patent applications, cited in this specification are herein incorporated by reference as if each individual publication were specifically and individually indicated to be incorporated by reference herein as though fully set forth.

The invention claimed is:

1. An isolated DNA molecule encoding the heavy and/or light chain(s) of a neutralising antibody which binds human IL-17, wherein the antibody comprises a heavy chain, which variable domain comprises a CDR having the sequence given in SEQ ID NO: 1 for CDR-H1, a CDR having the sequence given in SEQ ID NO: 2 for CDR-H2 and a CDR having the sequence given in SEQ ID NO: 3 for CDR-H3; and a light chain, which variable domain comprises a CDR having the sequence given in SEQ ID NO: 4 for CDR-L1, a CDR having the sequence given in SEQ ID NO: 5 for CDR-L2 and a CDR having the sequence given in SEQ ID NO: 6 for CDR-L3.

2. A cloning or expression vector comprising the DNA molecule according to claim 1.

3. The vector according to claim 2, wherein the vector comprises the sequences given in SEQ ID NO: 14 and SEQ ID NO: 18.

4. An isolated host cell comprising the cloning or expression vector according to claim 3.

5. A process for the production of a neutralising antibody, which binds human IL-17 and is encoded by the DNA molecules of SEQ ID NO:14 and 18, comprising culturing the host cell of claim 4 under conditions suitable for expression of the antibody, and isolating the antibody.

6. An isolated host cell comprising the cloning or expression vector according to claim 2.

* * * * *

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Gly Val Ile Phe Ser Asp Tyr Tyr Met Ala
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic

<400> SEQUENCE: 2

Ser Ile Asn Phe Asn Ala Asp Ile Ser Tyr Tyr Arg Glu Ser Val Lys
1               5                   10                  15

Gly

<210> SEQ ID NO 3
<211> LENGTH: 12
<212> TYPE: PRT
<213> ORGANISM: Artificial
<220> FEATURE:
<223> OTHER INFORMATION: Synthetic

<400> SEQUENCE: 3

Asp Ala Asn Arg Gln Asn Tyr Asp Trp Phe Ala Tyr
1               5                   10

<210> SEQ ID NO 4
<211> LENGTH: 15
<212> TYPE: PRT
<213> ORGANISM: Artificial
<220> FEATURE:
<223> OTHER INFORMATION: Synthetic

<400> SEQUENCE: 4

Lys Ala Ser Glu Ser Val Ser Ser Ser Met Tyr Ser Tyr Met His
1               5                   10                  15

<210> SEQ ID NO 5
<211> LENGTH: 7
<212> TYPE: PRT
<213> ORGANISM: Artificial
<220> FEATURE:
<223> OTHER INFORMATION: Synthetic

<400> SEQUENCE: 5

Arg Ala Ser Asn Leu Glu Ser
1               5

<210> SEQ ID NO 6
<211> LENGTH: 9
```

-continued

<210> SEQ ID NO 7
<211> LENGTH: 112
<212> TYPE: PRT
<213> ORGANISM: Artificial
<220> FEATURE:
<223> OTHER INFORMATION: Synthetic

<400> SEQUENCE: 7

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Glu Ser Val Ser Ser Ser
            20                  25                  30

Met Tyr Ser Tyr Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Trp
                85                  90                  95

Thr Ala Pro Arg Thr Phe Gly Gln Gly Thr Lys Val Glu Ile Lys Arg
            100                 105                 110
```

<210> SEQ ID NO 8
<211> LENGTH: 336
<212> TYPE: DNA
<213> ORGANISM: Artificial
<220> FEATURE:
<223> OTHER INFORMATION: Synthetic

<400> SEQUENCE: 8

```
gccatccagc tgacccagag cccttcctct ctcagcgcca gtgtcggaga cagagtgact      60
attacctgca aagcctccga atcagtcagt tcctctatgt attcttatat gcactggtac     120
cagcaaaagc ccggaaaggc tcctaaattg ctgatctaca gggcaagcaa cctcgagagc     180
ggcgtgccca gcaggttcag cggcagtggg tctggaactg actttaccct gacaatctcc     240
tcactccagc ccgaggactt cgccacctat tactgccagc agagctggac agctcctagg     300
acatttggac agggcactaa agtggaaatc aagcgt                              336
```

<210> SEQ ID NO 9
<211> LENGTH: 121
<212> TYPE: PRT
<213> ORGANISM: Artificial
<220> FEATURE:
<223> OTHER INFORMATION: Synthetic

<400> SEQUENCE: 9

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Gly Leu Glu Trp Val
```

```
                        35                  40                  45
Ala Ser Ile Asn Phe Asn Ala Asp Ile Ser Tyr Tyr Arg Glu Ser Val
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                 85                  90                  95

Thr Thr Asp Ala Asn Arg Gln Asn Tyr Asp Trp Phe Ala Tyr Trp Gly
                100                 105                 110

Gln Gly Thr Leu Val Thr Val Ser Ser
                115                 120

<210> SEQ ID NO 10
<211> LENGTH: 363
<212> TYPE: DNA
<213> ORGANISM: Artificial
<220> FEATURE:
<223> OTHER INFORMATION: Synthetic

<400> SEQUENCE: 10
gaggttcagc tcgttgaatc cggaggcgga ctcgtgaagc ccggaggcag tcttcgcttg    60
tcctgcgctg catctggagt gatctttagc gattactata tggcttgggt gagacaggca   120
cctgggaaag gcctcgaatg ggtggccagt attaacttca atgccgacat cagctactat   180
cgagagtctg tgaagggtag attcacaatc tcacgggatg acagtaagaa cacactgtac   240
ctgcagatga attccctgaa aaccgaggat accgccgttt actattgtac cactgacgcc   300
aacaggcaga attacgactg gtttgcctat tgggggcagg gcactctggt caccgtctcg   360
agc                                                                 363

<210> SEQ ID NO 11
<211> LENGTH: 218
<212> TYPE: PRT
<213> ORGANISM: Artificial
<220> FEATURE:
<223> OTHER INFORMATION: Synthetic

<400> SEQUENCE: 11

Ala Ile Gln Leu Thr Gln Ser Pro Ser Ser Leu Ser Ala Ser Val Gly
  1               5                  10                  15

Asp Arg Val Thr Ile Thr Cys Lys Ala Ser Glu Ser Val Ser Ser Ser
                 20                  25                  30

Met Tyr Ser Tyr Met His Trp Tyr Gln Gln Lys Pro Gly Lys Ala Pro
                 35                  40                  45

Lys Leu Leu Ile Tyr Arg Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Trp
                 85                  90                  95

Thr Ala Pro Arg Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
                130                 135                 140

Pro Arg Glu Ala Lys Val Gln Trp Lys Val Asp Asn Ala Leu Gln Ser
145                 150                 155                 160
```

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
210                 215

<210> SEQ ID NO 12
<211> LENGTH: 238
<212> TYPE: PRT
<213> ORGANISM: Artificial
<220> FEATURE:
<223> OTHER INFORMATION: Synthetic

<400> SEQUENCE: 12

Met Ser Val Pro Thr Gln Val Leu Gly Leu Leu Leu Leu Trp Leu Thr
1               5                   10                  15

Asp Ala Arg Cys Ala Ile Gln Leu Thr Gln Ser Pro Ser Ser Leu Ser
            20                  25                  30

Ala Ser Val Gly Asp Arg Val Thr Ile Thr Cys Lys Ala Ser Glu Ser
        35                  40                  45

Val Ser Ser Ser Met Tyr Ser Tyr Met His Trp Tyr Gln Gln Lys Pro
    50                  55                  60

Gly Lys Ala Pro Lys Leu Leu Ile Tyr Arg Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Ser Trp Thr Ala Pro Arg Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 13
<211> LENGTH: 657
<212> TYPE: DNA
<213> ORGANISM: Artificial
<220> FEATURE:
<223> OTHER INFORMATION: Synthetic

<400> SEQUENCE: 13
gccatccagc tgacccagag cccttcctct ctcagcgcca gtgtcggaga cagagtgact    60

-continued

```
attacctgca aagcctccga atcagtcagt tcctctatgt attcttatat gcactggtac      120
cagcaaaagc ccggaaaggc tcctaaattg ctgatctaca gggcaagcaa cctcgagagc      180
ggcgtgccca gcaggttcag cggcagtggg tctggaactg actttaccct gacaatctcc      240
tcactccagc ccgaggactt cgccacctat tactgccagc agagctggac agctcctagg      300
acatttggac agggcactaa agtggaaatc aagcgtacgg tagcggcccc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca cagggga gtgttag            657
```

<210> SEQ ID NO 14
<211> LENGTH: 717
<212> TYPE: DNA
<213> ORGANISM: Artificial
<220> FEATURE:
<223> OTHER INFORMATION: Synthetic

<400> SEQUENCE: 14

```
atgtcagttc ccacacaggt gctgggcctg cttctgttgt ggctcaccga tgctaggtgt       60
gccatccagc tgacccagag cccttcctct ctcagcgcca gtgtcggaga cagagtgact      120
attacctgca aagcctccga atcagtcagt tcctctatgt attcttatat gcactggtac      180
cagcaaaagc ccggaaaggc tcctaaattg ctgatctaca gggcaagcaa cctcgagagc      240
ggcgtgccca gcaggttcag cggcagtggg tctggaactg actttaccct gacaatctcc      300
tcactccagc ccgaggactt cgccacctat tactgccagc agagctggac agctcctagg      360
acatttggac agggcactaa agtggaaatc aagcgtacgg tagcggcccc atctgtcttc      420
atcttcccgc catctgatga gcagttgaaa tctggaactg cctctgttgt gtgcctgctg      480
aataacttct atcccagaga ggccaaagta cagtggaagg tggataacgc cctccaatcg      540
ggtaactccc aggagagtgt cacagagcag gacagcaagg acagcaccta cagcctcagc      600
agcaccctga cgctgagcaa agcagactac gagaaacaca agtctacgc ctgcgaagtc       660 acccatcagg gcctgagctc gcccgtcaca aagagcttca cagggga gtgttag            717
```

<210> SEQ ID NO 15
<211> LENGTH: 448
<212> TYPE: PRT
<213> ORGANISM: Artificial
<220> FEATURE:
<223> OTHER INFORMATION: Synthetic

<400> SEQUENCE: 15

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Phe Asn Ala Asp Ile Ser Tyr Tyr Arg Glu Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
```

```
                     85                  90                  95
Thr Thr Asp Ala Asn Arg Gln Asn Tyr Asp Trp Phe Ala Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 16
<211> LENGTH: 467
<212> TYPE: PRT
<213> ORGANISM: Artificial
<220> FEATURE:
<223> OTHER INFORMATION: Synthetic

<400> SEQUENCE: 16

Met Glu Trp Ser Trp Val Phe Leu Phe Phe Leu Ser Val Thr Thr Gly
1               5                   10                  15
```

-continued

```
Val His Ser Glu Val Gln Leu Val Glu Ser Gly Gly Leu Val Lys
         20                  25                  30
Pro Gly Gly Ser Leu Arg Leu Ser Cys Ala Ala Ser Gly Val Ile Phe
             35                  40                  45
Ser Asp Tyr Tyr Met Ala Trp Val Arg Gln Ala Pro Gly Lys Gly Leu
 50                  55                  60
Glu Trp Val Ala Ser Ile Asn Phe Asn Ala Asp Ile Ser Tyr Tyr Arg
 65                  70                  75                  80
Glu Ser Val Lys Gly Arg Phe Thr Ile Ser Arg Asp Asp Ser Lys Asn
                 85                  90                  95
Thr Leu Tyr Leu Gln Met Asn Ser Leu Lys Thr Glu Asp Thr Ala Val
            100                 105                 110
Tyr Tyr Cys Thr Thr Asp Ala Asn Arg Gln Asn Tyr Asp Trp Phe Ala
            115                 120                 125
Tyr Trp Gly Gln Gly Thr Leu Val Thr Val Ser Ser Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Lys Thr Tyr Thr Cys Asn
210                 215                 220
Val Asp His Lys Pro Ser Asn Thr Lys Val Asp Lys Arg Val Glu Ser
225                 230                 235                 240
Lys Tyr Gly Pro Pro Cys Pro Pro Cys Pro Ala Pro Glu Phe Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser Gln
            275                 280                 285
Glu Asp Pro Glu Val Gln Phe Asn Trp Tyr Val Asp Gly Val Glu Val
290                 295                 300
His Asn Ala Lys Thr Lys Pro Arg Glu Glu Gln Phe Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Gly Leu Pro Ser Ser Ile
            340                 345                 350
Glu Lys Thr Ile Ser Lys Ala Lys Gly Gln Pro Arg Glu Pro Gln Val
            355                 360                 365
Tyr Thr Leu Pro Pro Ser Gln Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Arg Leu Thr Val
            420                 425                 430
Asp Lys Ser Arg Trp Gln Glu Gly Asn Val Phe Ser Cys Ser Val Met
```

```
                435                 440                 445
His Glu Ala Leu His Asn His Tyr Thr Gln Lys Ser Leu Ser Leu Ser
            450                 455                 460

Leu Gly Lys
465
```

<210> SEQ ID NO 17
<211> LENGTH: 1954
<212> TYPE: DNA
<213> ORGANISM: Artificial
<220> FEATURE:
<223> OTHER INFORMATION: Synthetic

<400> SEQUENCE: 17

| | | | | | |
|---|---|---|---|---|---|
| gaggttcagc | tcgttgaatc | cggaggcgga | ctcgtgaagc | ccggaggcag | tcttcgcttg | 60 |
| tcctgcgctg | catctggagt | gatctttagc | gattactata | tggcttgggt | gagacaggca | 120 |
| cctgggaaag | gcctcgaatg | ggtggccagt | attaacttca | atgccgacat | cagctactat | 180 |
| cgagagtctg | tgaagggtag | attcacaatc | tcacgggatg | acagtaagaa | cacactgtac | 240 |
| ctgcagatga | attccctgaa | aaccgaggat | accgccgttt | actattgtac | cactgacgcc | 300 |
| aacaggcaga | attacgactg | gtttgcctat | tgggggcagg | gcactctggt | caccgtctcg | 360 |
| agcgcttcta | caagggccc | atccgtcttc | cccctggcgc | cctgctccag | gagcacctcc | 420 |
| gagagcacag | ccgccctggg | ctgcctggtc | aaggactact | cccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacgaag | 600 |
| acctacacct | gcaacgtaga | tcacaagccc | agcaacacca | aggtggacaa | gagagttggt | 660 |
| gagaggccag | cacagggagg | gagggtgtct | gctggaagcc | aggctcagcc | ctcctgcctg | 720 |
| gacgcacccc | ggctgtgcag | ccccagccca | gggcagcaag | catgcccca | tctgtctcct | 780 |
| caccccggagg | cctctgacca | ccccactcat | gcccagggag | agggtcttct | ggatttttcc | 840 |
| accaggctcc | gggcagccac | aggctggatg | cccctacccc | aggccctgcg | catacagggg | 900 |
| caggtgctgc | gctcagacct | gccaagagcc | atatccggga | ggaccctgcc | cctgacctaa | 960 |
| gcccaccca | aaggccaaac | tctccactcc | ctcagctcag | acaccttctc | tcctcccaga | 1020 |
| tctgagtaac | tcccaatctt | ctctctgcag | agtccaaata | tggtccccca | tgcccaccat | 1080 |
| gcccaggtaa | gccaacccag | gcctcgccct | ccagctcaag | gcgggacagg | tgccctagag | 1140 |
| tagcctgcat | ccagggacag | gccccagccg | ggtgctgacg | catccacctc | catctcttcc | 1200 |
| tcagcacctg | agttcctggg | gggaccatca | gtcttcctgt | tccccccaaa | acccaaggac | 1260 |
| actctcatga | tctcccggac | ccctgaggtc | acgtgcgtgg | tggtggacgt | gagccaggaa | 1320 |
| gaccccgagg | tccagttcaa | ctggtacgtg | gatggcgtgg | aggtgcataa | tgccaagaca | 1380 |
| aagccgcggg | aggagcagtt | caacagcacg | taccgtgtgg | tcagcgtcct | caccgtcctg | 1440 |
| caccaggact | ggctgaacgg | caaggagtac | aagtgcaagg | tctccaacaa | aggcctcccg | 1500 |
| tcctccatcg | agaaaaccat | ctccaaagcc | aaaggtggga | cccacggggt | gcgagggcca | 1560 |
| catggacaga | ggtcagctcg | gcccaccctc | tgccctggga | gtgaccgctg | tgccaacctc | 1620 |
| tgtccctaca | gggcagcccc | gagagccaca | ggtgtacacc | ctgccccat | ccaggagga | 1680 |
| gatgaccaag | aaccaggtca | gcctgacctg | cctggtcaaa | ggcttctacc | ccagcgacat | 1740 |
| cgccgtggag | tgggagagca | atgggcagcc | ggagaacaac | tacaagacca | cgcctcccgt | 1800 |

```
gctggactcc gacggctcct tcttcctcta cagcaggcta accgtggaca agagcaggtg    1860
gcaggagggg aatgtcttct catgctccgt gatgcatgag gctctgcaca accactacac    1920
acagaagagc ctctccctgt ctctgggtaa atga                                1954

<210> SEQ ID NO 18
<211> LENGTH: 2011
<212> TYPE: DNA
<213> ORGANISM: Artificial
<220> FEATURE:
<223> OTHER INFORMATION: Synthetic

<400> SEQUENCE: 18
atggaatggt cctgggtctt cctgtttttc ctttctgtca caaccggggt gcacagcgag      60
gttcagctcg ttgaatccgg aggcggactc gtgaagcccg gaggcagtct tcgcttgtcc     120
tgcgctgcat ctggagtgat ctttagcgat tactatatgg cttgggtgag acaggcacct     180
gggaaaggcc tcaatgggt ggccagtatt aacttcaatg ccgacatcag ctactatcga      240
gagtctgtga agggtagatt cacaatctca cgggatgaca gtaagaacac actgtacctg     300
cagatgaatt ccctgaaaac cgaggatacc gccgtttact attgtaccac tgacgccaac     360
aggcagaatt acgactggtt tgcctattgg gggcagggca ctctggtcac cgtctcgagc     420
gcttctacaa agggcccatc cgtcttcccc ctggcgccct gctccaggag cacctccgag     480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacgaagacc     660
tacacctgca acgtagatca caagcccagc aacaccaagg tggacaagag agttggtgag     720
aggccagcac agggagggag ggtgtctgct ggaagccagg ctcagccctc tgcctggac      780 gcaccccggc tgtgcagccc cagcccaggg cagcaaggca tgccccatct gtctcctcac     840
ccggaggcct ctgaccaccc cactcatgcc cagggagagg gtcttctgga ttttttccacc    900 aggctccggg cagccacagg ctggatgccc taccccagg ccctgcgcat acaggggcag      960
gtgctgcgct cagacctgcc aagagccata tccggagga ccctgcccct gacctaagcc      1020
caccccaaag gccaaactct ccactcccte agctcagaca ccttctctcc tcccagatct    1080
gagtaactcc caatcttctc tctgcagagt ccaaatatgg tccccccatgc ccaccatgcc   1140 caggtaagcc aacccaggcc tcgccctcca gctcaaggcg ggacaggtgc cctagagtag    1200
cctgcatcca gggacaggcc ccagccgggt gctgacgcat ccacctccat ctcttcctca    1260
gcacctgagt tcctgggggg accatcagtc ttcctgttcc ccccaaaacc caaggacact    1320
ctcatgatct cccggacccc tgaggtcacg tgcgtggtgg tggacgtgag ccaggaagac    1380
cccgaggtcc agttcaactg gtacgtggat ggcgtggagg tgcataatgc caagacaaag    1440
ccgcgggagg agcagttcaa cagcacgtac cgtgtggtca gcgtcctcac cgtcctgcac    1500
caggactggc tgaacggcaa ggagtacaag tgcaaggtct ccaacaaagg cctcccgtcc    1560
tccatcgaga aaaccatctc caaagccaaa ggtgggaccc acggggtgcg agggccacat    1620
ggacagaggt cagctcggcc caccctctgc cctgggagtg accgctgtgc caacctctgt    1680
ccctacaggg cagccccgag agccacaggt gtacaccctg cccccatccc aggaggagat    1740
gaccaagaac caggtcagcc tgacctgcct ggtcaaaggc ttctacccca gcgacatcgc    1800
cgtggagtgg gagagcaatg ggcagccgga gaacaactac aagaccacgc ctcccgtgct    1860
```

-continued

```
ggactccgac ggctccttct tcctctacag caggctaacc gtggacaaga gcaggtggca    1920 ggagggaat gtcttctcat gctccgtgat gcatgaggct ctgcacaacc actacacaca    1980
gaagagcctc tccctgtctc tgggtaaatg a                                  2011
```